United States Patent [19]

Wheeler

[11] 4,436,912

[45] Mar. 13, 1984

[54] 7-(2-(2-AMINOOXAZOL-4-YL)-2-(OX-IMINO)ACETAMIDO CEPHALOSPORIN ANTIBIOTICS AND INTERMEDIATES THEREFOR

[75] Inventor: William J. Wheeler, Indianapolis, Ind.

[73] Assignee: Eli Lilly and Company, Indianapolis, Ind.

[21] Appl. No.: 417,242

[22] Filed: Sep. 13, 1982

Related U.S. Application Data

[62] Division of Ser. No. 300,140, Sep. 8, 1981.

[51] Int. Cl.$^3$ .......................................... C07D 263/30
[52] U.S. Cl. .................................... 548/233; 548/236; 548/257; 548/473; 544/25; 544/21; 424/246
[58] Field of Search ....................... 548/233, 236, 257

[56] References Cited

U.S. PATENT DOCUMENTS 4,152,432  5/1979  Iteymes et al. ...................... 424/246
4,258,041  3/1981  O'Callaghan et al. .............. 424/246

*Primary Examiner*—Donald G. Daus
*Assistant Examiner*—G. Hendricks
*Attorney, Agent, or Firm*—Paul C. Steinhardt; Arthur R. Whale; William B. Scanlon

[57] ABSTRACT

Cephalosporin broad spectrum antibiotics possessing a 7β-[2-[(2-aminooxazol)-4-yl]-2-(substituted oximino]acetamido side chain and a variety of substituents at the 3-position of the cephalosporins are claimed. Also claimed are intermediates in the synthesis of the above cephalosporin antibiotics.

25 Claims, No Drawings

7-[2-(2-AMINOOXAZOL-4-yl)-2-(OX-IMINO)ACETAMIDO CEPHALOSPORIN ANTIBIOTICS AND INTERMEDIATES THEREFOR

This application is a division of application Ser. No. 300,140 filed Sept. 8, 1981.

BACKGROUND OF THE INVENTION

This invention relates to cephalosporin antibiotic compounds and intermediates in the synthesis thereof. In particular, it relates to cephalosporin compounds substituted in the 7-position with a 2-(2-aminooxazol-4-yl)-2-(substituted-oximino)acetamido group and in the 3-position with a variety of substituents, such as fluoro, chloro, bromo, hydroxy, acyloxymethyl, carbamoylmethyl, substituted and unsubstituted methyl pyridinium groups and heterocyclic thiomethyl groups containing 5- and 6-membered heterocyclic rings.

In recent years, much research has been done in the area of cephalosporins containing a 7-[2-(2-aminothiazol-4-yl]-2-(substituted oximino)acetamido side chain, with a wide variety of substitutents in the 3-position of the cephalosporin. Two of the most notable examples of such compounds are the potent antibiotics (a) sodium 7-[2-(2-aminothiazol-4-yl)-2-methoximinoacetamido]-3-acetoxy-3-cephem-4-carboxylate disclosed by Heymes, et al. in U.S. Pat. No. 4,152,432 and (b) the compound of the formula

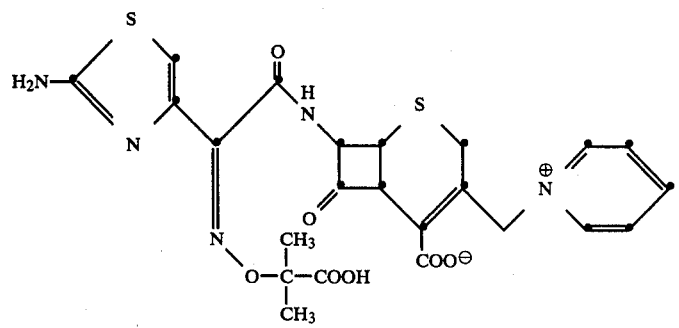

disclosed by O'Callahan et al. in U.S. Pat. No. 4,258,041.

The cephalosporin antibiotics of the instant invention possess excellent antibiotic activity while differing in structure from the aforementioned compounds and other compounds previously disclosed.

SUMMARY OF THE INVENTION

The cephalosporin antibiotics and cephalosporin intermediates of this invention are represented by the following general formula A.

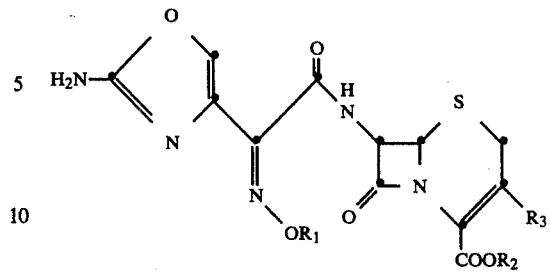

wherein $R_1$ can be hydrogen, $C_1$ to $C_4$ alkyl or a group of the formula

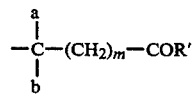

wherein R' can be, e.g., hydroxy, alkoxy, amino, substituted amino and m is 0 to 3, $R_2$ can be hydrogen, a pharmaceutically acceptable, non-toxic salt, the hydrates of said salt, or the non-toxic metabolically labile esters thereof; $R_3$ can be hydrogen, halo, hydroxy, methoxy, lowr acyloxyoxymethyl, a group of the formula

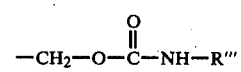

a methyl pyridinium group of the formula

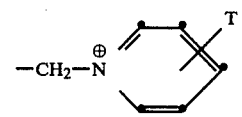

or a heterocyclic thiomethyl group, wherein the heterocyclic ring can be a 5- or 6-membered ring at least one nitrogen and up to 3 other heteroatoms chosen from nitrogen, sulfur or oxygen.

A second aspect of this invention is an intermediate oxime side chain of the general formula B

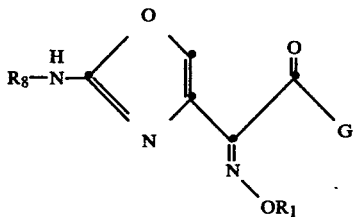

wherein $R_1$ is the same as in general formula A; G is chloro, bromo, hydroxy, lower alkoxy, phenoxy, a group of the formula —O—J wherein J is the residue of a group forming an activated ester, or a group of the formula —O$^\ominus$ M$^\oplus$ wherein M$^\oplus$ is a monovalent cation and $R_8$ is hydrogen or an amino protecting group.

DETAILED DESCRIPTION OF THE INVENTION

This invention is directed to cephalosporin compounds of the following general formula

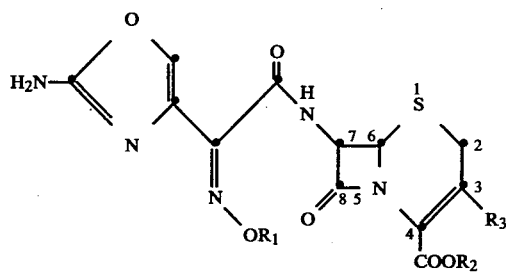

This invention is also directed to an intermediate used in the synthesis of the above cephalosporin compounds. The intermediate compound has the general formula

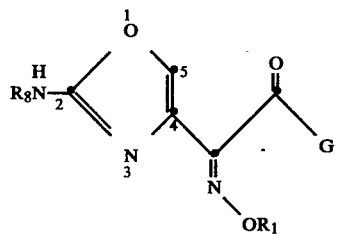

and for convenience sake will be referred to in the instant application as the "oxime sidechain".

In the formulas contained in this application, the mark "◂▬" indicates the β-configuration and the hash line "||||" indicates the α-configuration. Also, in the formulas contained in this application the geometrical isomer of the oxime function indicated by the following partial formula

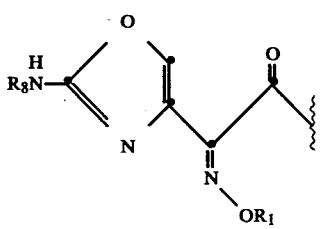

is referred to as the "Z" or "syn" isomer, while the opposite isomer, represented by the following partial formula

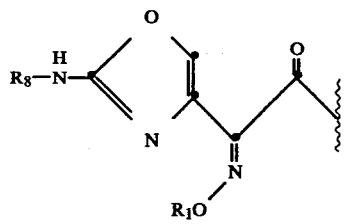

is referred to as the "E" or "anti" isomer.

It will be understood that since the cephalosporins and the oxime sidechain intermediates of this invention are geometrical isomers, some admixture between the Z isomer and the corresponding E isomer may occur.

The cephalosporin compounds of this invention are represented by the following general formula I

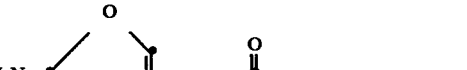

wherein:

$R_1$ is hydrogen, $C_1$ to $C_4$ alkyl, a carboxy-substituted alkyl or carboxy-substituted cycloalkyl group represented by the formula

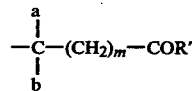

wherein m is 0 to 3, a and b when taken separately are independently hydrogen or $C_1$ to $C_3$ alkyl, or when taken together with the carbon to which they are attached form a $C_3$ to $C_7$ carbocyclic ring; R' is hydroxy, amino, $C_1$ to $C_4$ alkoxy, or —OR", where R" is a carboxy protecting group; or $R_1$ is a secondary amido group of the formula

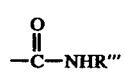

wherein R''' is $C_1$ to $C_4$ alkyl, phenyl or $C_1$ to $C_3$ alkyl substituted by phenyl; $R_2$ is hydrogen, a carboxy protecting group or a pharmaceutically acceptable, non-toxic salt thereof, the hydrates of said salt, or the non-toxic metabolically labile esters thereof; $R_3$ is (a) hydrogen, fluoro, bromo, chloro, hydroxy, or methoxy; or (b) ($C_2$ to $C_4$ acyloxy)methyl; or (c) a methyl carbamate group of the formula

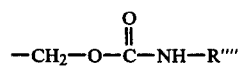

wherein R'''' is hydrogen or $C_1$ to $C_4$ alkyl; or
(d) a methyl pyridinium group of the formula

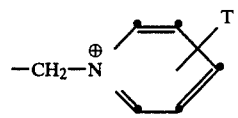

wherein T is
(i) hydrogen, trifluoromethyl, $C_1$ to $C_4$ alkyl, $C_1$ to $C_4$ alkoxy, hydroxy, cyano, halo or hydroxymethyl; or
(ii) carboxy, $C_1$-$C_4$ alkoxycarbonyl, $C_1$ to $C_4$ alkanoyl or $C_1$ to $C_4$ alkanoyloxy; or
(iii) an amido group of the formula

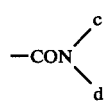

wherein c is hydrogen, methyl, ethyl or cyclopropyl and d is hydrogen, methyl or ethyl; or
(iv) a group of the formula

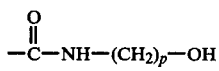

wherein p is 2 to 4; provided that: (a) when the pyridinium ring is substituted with the above substituents in (iv), the pyridinium ring is additionally substituted with $R_4$, wherein $R_4$ is hydrogen or $C_1$ to $C_4$ alkyl; and (b) when T is hydroxy or halo T is only bonded to the 3-position of the pyridinium ring; or
(e) a heterocyclic thiomethyl group of the formula —$CH_2$—S—Y, wherein Y is

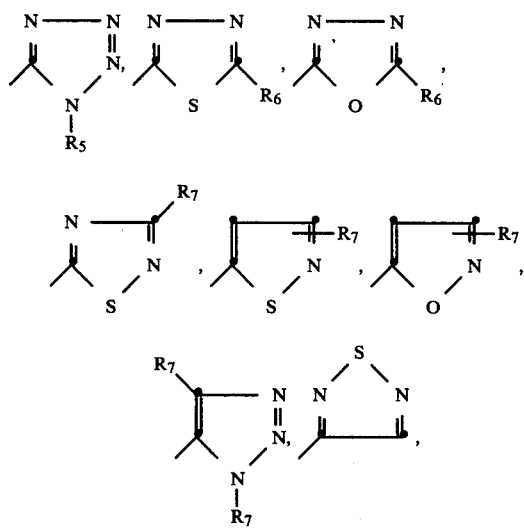

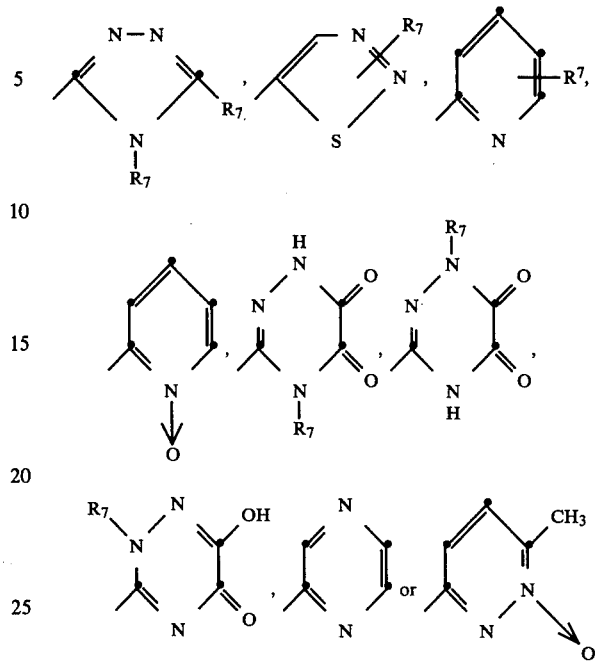

wherein
$R_5$ is hydrogen, $C_1$ to $C_4$ alkyl, —$CH_2COOH$, or —$CH_2SO_3H$;
$R_6$ is hydrogen, $C_1$ to $C_4$ alkyl, phenyl or amino; and
$R_7$ is hydrogen or $C_1$ to $C_4$ alkyl;
provided that, when $R_2$ is hydrogen, $R_3$ is not hydroxy.

In the foregoing definitions of the cephalosporin compounds, the term "$C_1$ to $C_4$ alkyl" means methyl, ethyl, propyl, isopropyl, butyl, sec-butyl or tert-butyl.

The term "$C_1$ to $C_3$ alkyl" means methyl, ethyl, propyl or iso-propyl.

The term "$C_1$ to $C_4$ alkoxy" refers to methoxy, ethoxy, n-propoxy, iso-propoxy, sec-butoxy, n-butoxy and the like.

With respect to the term $R_1$ in Formula I, the carboxy-substituted alkyl group (R' is hydroxy) represented by the formula

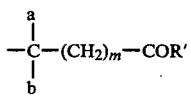

is illustrated by carboxymethyl, 2-carboxyethyl, 1-carboxyethyl, 3-carboxypropyl, 2-carboxypropyl, 4-carboxybutyl, 3-carboxypentyl, 4-carboxyheptyl, 2-carboxybutyl, and the like. When a and b are taken together, examples of the carboxy-substituted $C_3$-$C_7$ carbocyclic rings are 1-carboxycycloprop-1-yl, 1-carboxycyclobut-1-yl, 1-carboxymethylcyclobut-1-yl, 1-carboxycyclopent-1-yl, 1-carboxycyclohex-1-yl, 1-carboxycyclohep-1-yl, 1-carboxyethylcyclopent-1-yl, 1-carboxypropylcyclohex-1-yl, and the like. Examples of such groups when R' is amino are aminocarbonylmethyl, 2-aminocarbonylethyl, 3-aminocarbonylpropyl, 2-aminocarbonylprop-2-yl, 1-aminocarbonylcycloprop-1-yl, 1-aminocarbonylcyclohex-1-yl, and like carboxamido substituted alkyl and cycloalkyl groups.

Examples of such groups when R' is $C_1$ to $C_4$ alkoxy are ethoxycarbonylmethyl, methoxycarbonylpropyl, 2-ethoxycarbonylprop-2-yl, 5-butyloxycarbonylmethyl, 3-ethoxycarbonylpropyl, 1-ethoxycarbonylcyclobut-1-yl, 1-(methoxycarbonylmethyl)cyclopent-1-yl, and like groups.

It will be appreciated by those skilled in the art that when a and b in the above formula represent different $C_1$ to $C_3$ alkyl groups, the carbon atom to which they are attached comprise a center of asymmetry. Such compounds are diastereometric and the present invention embraces individual diastereomers of these compounds as well as mixtures thereof.

Illustrative of the secondary amido groups at $R_1$ are N-methylcarbamoyl, N-ethylcarbamoyl, N-phenylcarbamoyl, N-benzylcarbamoyl, N-(2-phenylethyl)-carbamoyl, and the like.

The term "carboxy protecting group" indicates a carboxy group which has been esterified with one of the more commonly used carboxylic acid protecting ester groups employed to block or protect the carboxylic acid functionality while reactions involving other functional sites of the compound are carried out. Such carboxy protecting groups may be subsequently removed by any of the appropriate methods disclosed in the literature, for example acid or base catalyzed hydrolysis, hydrogenolysis, and enzymatically catalyzed hydrolysis to yield the free carboxylic acid. Examples of such carboxylic acid group include 2-iodoethyl, tert-butyl, 2,2,2-trichloroethyl, 4-methoxybenzyl, 4-nitrobenzyl, diphenylmethyl, 4-methoxydiphenylmethyl, 4,4'-dimethoxydiphenylmethyl benzyl, trialkylsilyl, 2,4,6-trimethoxybenzyl, trityl, 4-methoxytrityl, 4,4'-dimethoxytrityl, 4,4',4"-trimethoxytrityl and like ester forming moieties. The nature of such ester forming groups is not critical so long as the ester formed therewith is stable under the reaction conditions of a reaction on another position of the molecule.

In the above definition, the term "carboxy protecting group" is not exhaustively defined. The function of such groups is to protect the reactive functional groups during the preparation of the desired products and then be removed without disrupting the remainder of the molecule. Many such protecting groups are well known in the art and the use of other groups equally applicable to the synthesis of the compounds of the present invention, such as those described in Ch. 5 of J. F. W. McOmie, "Protective Groups in Organic Chemistry", Plenum Press, 1973, will be recognized as suitable. Thus, there is no novelty or inventiveness asserted with regard to the "carboxy protecting groups" described in this specification.

The term "pharmaceutically acceptable, non-toxic salt", refers to the inorganic salts of the above compounds formed with the alkali and alkaline earth metals such as lithium, sodium, potassium, barium and calcium, organic base salts such as ammonium, dibenzylammonium, benzylammonium, 2-hydroxyethylammonium, bis(2-hydroxyethyl)ammonium, phenylethylbenzylamine, dibenzylethylenediamine, and like salts. Other amine salts can be formed with procaine, quinine and N-methylglusoamine, plus salts formed with basic amino acids such as glycine, ornithine, histidine, phenylglycine, lysine and arginine. These salts are useful in preparing suitable pharmaceutical compositions of the instant compounds for therapeutic purposes. Because of the basic amino group in the position of the oxazole ring moiety, the compounds of the instant invention form acid addition salts with suitable acids such as hydrochloric acid, hydrobromic acid, phosphoric acid, sulfuric acid, the organic sulfonic acids, e.g. methanesulfonic acid, benzenesulfonic acid, toluenesulfonic acid, and like acids. The acid addition salts also may be used for preparing suitable pharmaceutical compositions of the instant compounds. In addition, when $R_3$ is a group of the formula

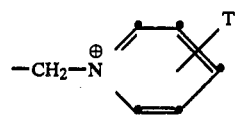

the $R_2$ group will be a carboxy anion, in other words, the molecules will exist in the pharmaceutically acceptable betaine form.

The hydrates of the above salts are also encompassed by the scope of the instant invention.

The term "non-toxic metabolically labile esters" refers to those biologically active ester forms which conduct, for example, to increase the blood levels and prolong the efficacy of such ester compounds. Such ester groups include lower alkoxymethyl groups, e.g. methoxymethyl, ethoxymethyl, isopropoxymethyl, α-methoxyethyl, groups such as α-lower alkoxy ($C_1$ to $C_4$) ethyl; e.g. methoxyethyl, ethoxyethyl, propoxyethyl, iso-propoxyethyl, etc; $C_1$ to $C_3$ alkylthiomethyl groups, e.g. methylthiomethyl, ethylthiomethyl, isopropylthiomethyl, etc; acyloxymethyl groups, e.g. pivaloyloxymethyl, α-acetoxymethyl, etc; ethoxycarbonyl-1-methyl; or α-acyloxy-α-substituted methyl groups, e.g. α-acetoxy-α-methyl-methyl.

When $R_3$ is "$C_2$ to $C_4$ acyloxymethyl" we mean organic moieties such as acetoxymethyl, propionyloxymethyl and butyryloxymethyl.

Examples of the methyl carbamate group of $R_3$ include carbamoylmethyl, N-methylcarbamoylmethyl, N-butylcarbamoylmethyl, N-propylcarbamoylmethyl, N-(iso-propyl)carbamoylmethyl, N-butylcarbamoylmethyl, N-(sec-butyl)carbamoylmethyl and N-(tert-butylcarbamoylmethyl).

When, in the Formula I, $R_3$ is a pyridinium group, the terms represented by "T" are exemplified as follows:

the term "$C_1$ to $C_4$ alkoxycarbonyl" refers to the methyl, ethyl, propyl, iso-propyl, butyl, sec-butyl and tert-butyl esters of a carboxylic acid, which acid is in turn bound to a pyridinium ring. Analogously, the term "$C_1$ to $C_4$ alkanoyl" refers to the formyl, acetyl, propionyl, iso-propionyl, butyryl, sec-butyryl and the tert-butyryl groups, which are bound through the carbonyl group to a pyridinium ring. Finally, by the term "$C_1$ to $C_4$ alkanoyloxy" refers to the formyloxy, acetyloxy, propionyloxy iso-propionyloxy, butyryloxy, sec-butyryloxy and tert-butyryloxy groups that are bound through the $sp^3$ hydridized oxygen to the pyridinium ring.

By the term "halo" we mean fluoro, chloro, bromo or iodo.

The instant invention embraces compounds where the pyridinium group at $R_3$ is monosubstituted at ring positions 2 through 6 with any of the substituents listed for the methyl pyridinium group in claim 1, provided that, when T is halo or hydroxy, T is bonded only to the 3-position of the pyridinium ring. Examples of pyridinium groups that are in turn bound to a 3'-methylene moiety at $R_3$ include: pyridinium, 4-trifluoromethylpyridinium, 3-trifluoromethypyridinium, 2-methylpyridinium, 4-methylpyridinium, 3-ethylpyridinium, 4-propylpyridinium, 4-butylpyridinium, 3-methoxypyridinium, 4-methoxypyridinium, 2-methoxypyridinium, 4-ethoxypyridinium, 3-ethoxypyridinium, 4-iso-propoxypyridinium, 3-sec-butoxypyridinium, 4-butoxypyridinium, 3-hydroxypyridinium, 4-cyanopyridinium, 3-cyanopyridinium, 3-chloropyridinium, 3-iodopyridinium, 4-(hydroxymethyl)pyridinium, 3-(hydroxymethyl)pyridinium, 4-carboxypyridinium, 4-carbomethoxypyridinium, 3-carbomethoxypyridinium, 2-carbomethoxypyridinium, 4-carboethoxypyridinium, 3-carbopropoxypyridinium, 4-carbobutoxypyridinium, 4-formylpyridinium, 2-formylpyridinium, 3-formylpyridinium, 4-acetylpyridinium, 3-acetylpyridinium, 4-propionylpyridinium, 4-tert-butyrylpyridinium, 3-butyrylpyridinium, 3-formyloxypyridinium, and 3-iso-propionyloxypyridinium.

It should be noted that the amido substituent of the methyl pyridinium group, represented by the formula

may be substituted, monosubstituted or disubstituted, as defined, and, in the disubstituted embodiments, the N-substituents may be the same or different.

Examples of amido-substituted methyl pyridinium ring include N-methyl pyridinium-4-carboxamide, pyridinium-3-carboxamide, pyridinium-4-carboxamide, N-cyclopropyl pyridinium-3-carboxamide, N-methyl-N-ethyl pyridinium-3-carboxamide, N,N-dimethylpyridinium-3-carboxamide, N-ethyl pyridinium-4-carboxamide and the like.

Examples of a methyl pyridinium group substituted with a group of the formula

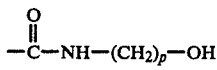

include N-(hydroxymethyl)pyridinium-3-carboxamido, N-(hydroxymethyl)pyridinium-4-carboxamido, N-(hydroxyethyl)pyridinium-3-carboxamido, N-(hydroxypropyl)pyridinium-4-carboxamido, N-(hydroxybutyl)pyridinium-3-carboxamido and the like. The preferred amido substituted pyridiniums are the N-(hydroxymethyl)pyridinium-3-carboxamido and the N-(hydroxymethyl)pyridinium-4-carboxamido.

Examples of heterocyclic groups Y when, in Formula I, $R_3$ is a heterocyclic thiomethyl group —CH$_2$—S—Y are 1H-tetrazol-5-yl, 1-methyl-1H-tetrazol-5-yl, 1-(n-propyl)-1H-tetrazol-5-yl, 1-(sec-butyl)-1H-tetrazol-5-yl, 1-(2-acetic acid)-1H-tetrazol-5-yl, 1-(methylsulfonic acid)-1H-tetrazol-5-yl, 5-amino-1,3,4-thiadiazol-2-yl, 5-phenyl-1,3,4-thiadiazol-2-yl, 5-methyl-1,3,4-thiadiazol-2-yl, 5-ethyl-1,3,4-thiadiazol-2-yl, 5-(n-butyl)-1,3,4-thiadiazol-2-yl, 1,3,4-oxadiazol-2-yl, 5-phenyl-1,3,4-oxadiazol-2-yl, 5-amino-1,3,4-oxadiazol-2-yl, 5-methyl-1,3,4-oxadiazol-2-yl, 5-(iso-propyl)-1,3,4-oxadiazol-2-yl, 5-(tert-butyl)-1,3,4-oxadiazol-2-yl, 1,2,4-thiadiazol-2-yl, 3-methyl-1,2,4-thiadiazol-5-yl, 3-ethyl-1,2,4-thiadiazol-5-yl, 3-(n-butyl)-1,2,4-thiadiazol-5-yl, isothiazol-5-yl, 3-methylisothiazol-5-yl, 4-methylisothiazol-5-yl, 3-ethyl-isothiazol-5-yl, 4-(n-propyl)-isothiazol-5-yl, 3-(iso-propyl)-isothiazol-5-yl, 4-(n-butyl)-isothiazol-5-yl, 3-(sec-butyl)-isothiazol-5-yl, isoxazol-5-yl, 3-methyl-isoxazol-5-yl, 4-methylisoxazol-5-yl, 3-ethyl-isoxazol-5-yl, 4-ethyl-isoxazol-5-yl, 3-(n-propyl)-isoxazol-5-yl, 4-(iso-propyl)-isoxazol-5-yl, 4-(n-butyl)-isoxazol-5-yl, 3-(sec-butyl)-isoxazol-5-yl, 1H-1,2,3-triazol-5-yl, 1-methyl-1H-1,2,3-triazol-5-yl, 4-methyl-1H-1,2,3-triazol-5-yl, 1,4-dimethyl-1H-1,2,3-triazol-5-yl, 1-ethyl-1H-1,2,3-triazol-5-yl, 4-ethyl-1H-1,2,3-triazol-5-yl, 1,4-diethyl-1H-1,2,3-triazol-5-yl, 1-(n-propyl)-1H-1,2,3-triazol-5-yl, 4-(iso-propyl)-1H-1,2,3-triazol-5-yl, 1,4-(di-n-butyl)-1H-1,2,3-triazol-5-yl, 1-(sec-butyl)-1H-1,2,3-triazol-5-yl, 1,2,5-thiadiazol-3-yl, 1,3,4-triazol-5-yl, 1-methyl-1,3,4-triazol-5-yl, 1-ethyl-1,3,4-triazol-5-yl, 1-(n-butyl)-1,3,4-triazol-5-yl, 2-methyl-1,3,4-triazol-5-yl, 2-ethyl-1,3,4-triazol-5-yl, 2-propyl-1,3,4-triazol-5-yl, 1,2-dimethyl-1,3,4-triazol-5-yl, 1,2-(di-n-butyl)-1,3,4-triazol-5-yl, 1-methyl-2-ethyl-1,3,4-triazol-5-yl, 1-ethyl-2-methyl-1,3,4-triazol-5-yl, 1-propyl-2-methyl-1,3,4-triazol-5-yl, 1,2,3-thiadiazol-5-yl, 4-methyl-1,3,4-thiadiazol-5-yl, 4-ethyl-1,2,3-thiadiazol-5-yl, 4-propyl-1,2,3-thiadiazol-5-yl, 4-butyl-1,2,3-thiadiazol-5-yl, pyridin-6-yl, 2-methylpyridin-6-yl, 3-methylpyridin-6-yl, 4-methylpyridin-6-yl, 5-methylpyridin-6-yl, 2-ethylpyridin-6-yl, 4-ethylpyridin-6-yl, 3-ethylpyridin-6-yl, 2-(n-propyl)pyridin-6-yl, 3-(n-propyl)pyridin-6-yl, 4-(iso-propyl)-pyridin-6-yl, 2-(n-butyl)pyridin-6-yl, 4-(sec-butyl)pyridin-6-yl, pyridin-6-yl-N-oxide, 1,6,4,5-tetrahydro-5,6-dioxo-4-methyl-as-triazin-3-yl, 1,6,4,5-tetrahydro-5,6-dioxo-as-triazin-3-yl, 1,6,4,5-tetrahydro-5,6-dioxo-4-ethyl-as-triazin-3-yl, 1,6,4,5-tetrahydro-5,6-dioxo-4-(n-propyl)-as-triazin-3-yl, 1,6,4,5-tetrahydro-5,6-dioxo-4-(n-butyl)-as-triazin-3-yl, 1,6,4,5-tetrahydro-5,6-dioxo-1-methyl-as-triazin-3-yl, 1,6,4,5-tetrahydro-5,6-dioxo-1-ethyl-as-triazin-3-yl, 1,6,4,5-tetrahydro-5,6-dioxo-1-(iso-propyl)-as-triazin-3-yl, 1,6,4,5-tetrahydro-5,6-dioxo-1-(n-butyl)-as-triazin-3-yl, 2,5-dihydro-5-oxo-6-hydroxy-as-triazin-3-yl, 2,5-dihydro-5-oxo-6-hydroxy-2-methyl-as-triazin-3-yl, 2,5-dihydro-5-oxo-6-hydroxy-2-ethyl-as-triazin-3-yl, 2,5-dihydro-5-oxo-6-hydroxy-(2-n-propyl)-as-triazin-3-yl, 2,5-dihydro-5-oxo-6-hydroxy-(2-n-butyl)-as-triazin-3-yl, pyrazin-2-yl, 3-methyl-2-(N-oxide)-pyridizin-6-yl, and like heterocycles.

Preferred heterocycles are 1-methyl-1H-tetrahydro-5-yl, 5-methyl-1,3,4-thiadiazol-2-yl, 2,5-dihydro-5-oxo-6-hydroxy-2-methyl-as-triazin-3-yl and 1,6,4,5-tetrahydro-5,6-dioxo-4-methyl-as-triazin-3-yl.

Finally, a proviso in the description of the above cephalosporin is that when $R_3$ is hydroxy, $R_2$ can be anything defined except hydrogen.

The intermediate oxide side compound of this invention has the following general formula

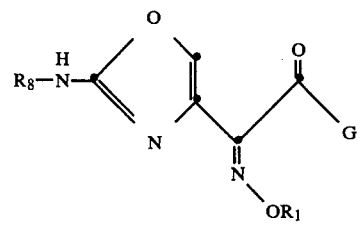

wherein $R_1$ has the same meaning as defined for Formula I; G is chloro, bromo, hydroxy, $C_1$ to $C_4$ alkoxy, phenoxy or a group of the formula

—O—J wherein J is the residue of a group forming an activated ester; or a group of the formula

—O⁻M⊕ wherein M⊕ is a monovalent cation; and R₈ is hydrogen or an amino protecting group.

The term "active ester" used in the above Formula II refers to the ester group $$-\overset{O}{\underset{\|}{C}}-O-J$$

where J is p-nitrophenol, 2,4-dinitrophenyl, pentachlorophenyl, molecules of the formula

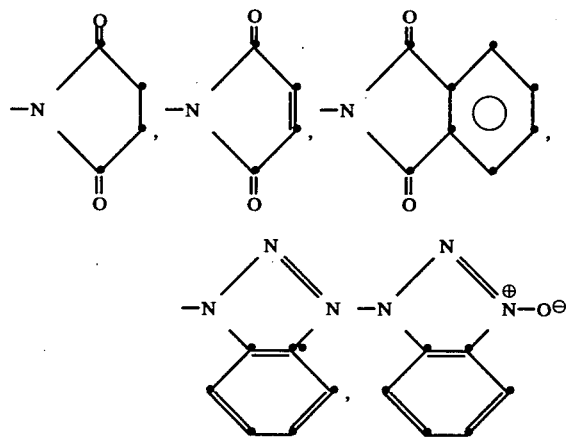

and the like. The term also includes acid anhydrides and mixed acid anhydrides (ie., where

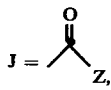

and Z is a substituent bound to the carbonyl through a carbon or an oxygen).

The mixed acid anhydride is exemplified by the mixed anhydrides with carbonic acid monoesters such as monomethyl carbonate, monoisobutyl carbonate, etc. and the mixed anhydrides with lower alkanoic acids which may optionally be substituted by halogen, such as pivalic acid, trichloroacetic acid, etc. The preferred active ester groups the following benzotriazole groups that is, where J is

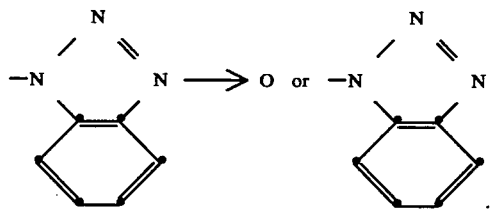

The most preferred of the active ester groups is the former of the above two more preferred benzotriazole groups.

By the term "monovalent cation" we mean cations such as the lithium, sodium and potassium cations, and the like, and the ammonium cations such as ammonium, dibenzylammonium, benzylammonium, phenylethylbenzylammonium, 2-hydroxyethylammonium, and the like.

In the above Formula II, when R₈ is an "amino protecting group", I mean examples such as aromatic acyl groups, e.g. phthaloyl, benzoyl, benzoyl group substituted with halogen, nitro or lower alkyls of 1 to 4 carbon atoms (e.g. chlorobenzyl, p-nitrobenzyl, p-tert-butylbenzoyl, toluoyl, etc.), naphthyl, phenylacetyl, phenoxyacetyl, benzenesulfonyl and benzenesulfonyl group substituted with lower alkyls of 1 to 4 carbon atoms (e.g. p-tert-butylbenzenesulfonyl, toluenesulfonyl, etc.), camphorsulfonyl, methanesulfonyl, acyl groups derived from aliphatic or halogenated aliphatic carboxylic acids such as acetyl, valeryl, n-decanoyl, acryloyl, pivaloyl, halogenoacetyl (e.g. monochloroacetyl, monobromoacetyl, dichloroacetyl, trichloroacetyl, etc.); esterified carboxyls such as ethoxycarbonyl, tert-butyloxycarbonyl, isobornyloxycarbonyl, phenyloxycarbonyl, trichloroethoxycarbonyl, benzyloxycarbonyl, carbamoyl groups such as methylcarbamoyl, phenylcarbamoyl, naphthylcarbamoyl, etc., the corresponding thiocarbamoyl groups. N-mono-, di- and trihalogenoacetylcarbamoyloxy groups such as N-chloroacetylcarbamoyloxy, N-chlorosulfonylcarbamoyloxy, N-trimethylsilylcarbamoyloxy, etc., the phenylglycyloxy group, and di- and trialkyl silyl protecting groups such as the trimethylsilyl group. The nature of the amino protecting group is not critical so long as the protected amino group survives the reaction condition while carrying out a reaction on another part of the molecule, and that subsequently the protecting group can be removed without disrupting the structure of the rest of the molecule.

The preferred amino protecting group is 2-chloroacetyl.

It should be noted that R₈ need only be an amino protecting group when the methoxy ester is being cleaved during the synthesis of the compound of Formula II, and need not be protected when the compound of Formula III is acylated with the compound of Formula II, as discussed below.

The preferred method of synthesis for the compounds of Formula I of the instant application involves acylating a compound of the Formula III

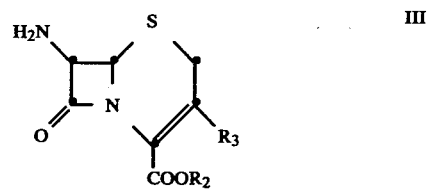

with the intermediate oxime side chain of Formula IV

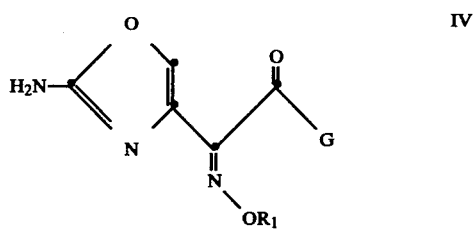

wherein $R_1$, $R_2$, $R_3$ and G have the same meanings as described before.

In this preferred method of synthesis the desired $R_3$ group is in place before the acylation reaction is carried out.

The preferred variation for carrying out the above acylation reaction occurs when G is a group of the formula

—O—J wherein J is the residue of a group forming an activated ester. Preferred groups at J are

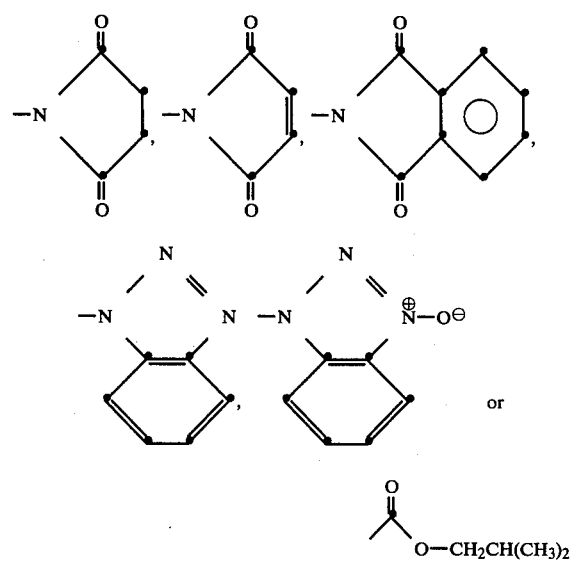

with the latter two groups (the 1-N-oxide benzotriazole and isobutyloxycarbonyl) being more preferred, and the 1-N-oxide benzotriazole moiety being most preferred.

Alternatively, when G in Formula IV is hydroxy or the salt form thereof, the oxime side chain is coupled with the 7-amino nucleus (Formula III) via N-acylation employing a suitable condensing agent. The condensing agent is exemplified by N,N'-disubstituted carbodiimides such as N,N'-dicyclohexylcarbodiimide, N,N'-diethylcarbodiimide, N,N'-di-n-propylcarbodiimide, N,N'-diisopropylcarbodiimide, N,N'-diallylcarbodiimide, N,N'-bis(p-dimethylaminophenyl)carbodiimide, N-ethyl-N'-(4''-ethylmorpholinyl)carbodiimide and the like, other suitable carbodiimides being disclosed by Sheehan in U.S. Pat. No. 2,938,892 and by Hofmann et al. U.S. Pat. No. 3,065,224; azolides such as N,N'-carbonylimidazole, N,N'-thionyldiimidazol, etc.; dehydrating agents such as N-ethoxycarbonyl-2-ethoxy-1,2-dihydroquinoline, phosphorus oxychloride, alkoxyacetylene, etc., and 2-halogenopyridinium salts (such as 2-chloropyridinium methyl iodide, 2-fluoropyridinium methyl iodide, etc.). Specific examples of the above acylation reaction can be found in the Experimental section.

In addition, the above preferred method of synthesis for the cephalosporin compound in Formula I can also be carried out when G is chloro or bromo.

When G is $C_1$ to $C_4$ alkoxy or phenoxy in the above Formula IV, these esters can be converted to the active esters, the carboxylic acid or carboxylate salt or the acyl chloride or bromide by methods well known in the art to facilitate acylation the cephalosporin nucleus, represented by Formula III above.

An alternative synthesis for the compounds of Formula I, wherein $R_3$ is a methyl pyridinium group of the formula

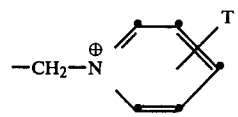

or a heterocyclic thiomethyl group of the formula

—$CH_2$—S—Y (where T and Y are as described for Formula I), entails the reaction of a 3-halomethylcephalosporin, represented by the Formula V

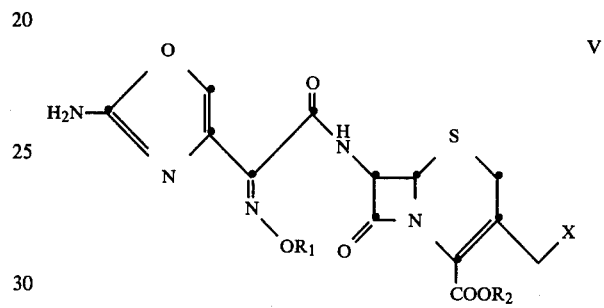

wherein $R_1$ and $R_2$ are as defined above for Formula I and X is chloro, bromo or iodo, with a pyridine moiety of the formula

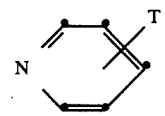

or a heterocyclic mercaptide moiety, (derived from the above heterocyclic thiol moieties of the formula H—S—Y), of the formula $M^{\oplus\ominus}S$—Y Preferably, X is iodo and $R_2$ is a trialkyl silyl group such as tri($C_1$ to $C_4$ alkyl)silyl ester, for example, trimethylsilyl or triethylsilyl.

It is also desirable that nucleophilic substituents on the pyridine and on the heterocyclic mercaptide moieties, such as carboxy, hydroxy and sulfonic acid functions, be suitably protected so that these substituents do not interfere with the displacement reaction by the nitrogen of the pyridine or the sulfur of the heterocyclic mercaptide. These protecting groups can be removed once the displacement reaction is carried out.

The 3-halomethyl substituted compounds can be prepared by methods known in the art, for example, by the acylation of a 3-halomethyl-7-amino-3-cephem nucleus compound. The preferred 3-iodomethyl compounds of the Formula 2 are best obtained by the method described by R. Bonjouklian, U.S. Pat. No. 4,266,049. According to this method, a 7-acylamido-3-acetoxymethyl-3-cephem-4-carboxylic acid is first silylated to block reactive groups such as the $C_4$ carboxylic acid group and the silylated derivative is reacted with a trialkylsilyliodide, e.g. trimethylsilyliodide (TMSI), to form the 3-iodomethyl silylated derivative. The latter is then reacted with the above pyridine or the above heterocyclic mercaptide and the silyl blocks are hydrolyzed to provide a compound of the Formula I. The preparation of compounds of the Formula 1 by this method is illustrated by the following general reaction Scheme I:

Scheme I

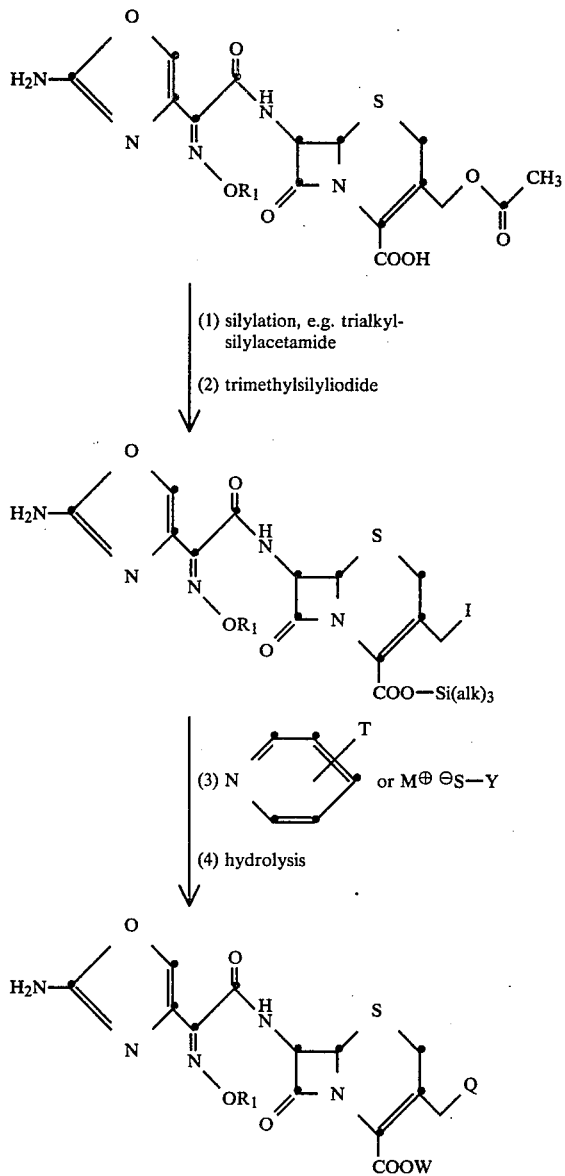

(1) silylation, e.g. trialkyl-silylacetamide (2) trimethylsilyliodide (3) N 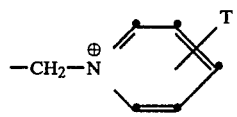 or M⊕ ⊖S—Y (4) hydrolysis In the above Scheme, when

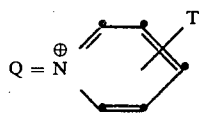

W is a negative charge, and when Q=S—Y, W is hydrogen.

The reaction is carried out with either the pyridine or the heterocyclic thiol at a temperature between about 20° C. and about 45° C. in an inert aprotic organic solvent under substantially anhydrous conditions. The reaction in either case is conveniently carried out at ambient temperature or at slightly elevated temperatures. Solvents which can be used with the pyridines and the thiols are, for example, acetonitrile, propionitrile, dimethylformamide, dimethylacetamide and like commonly used aprotic solvents.

Alternatively, the compounds of Formula I, wherein $R_3$ is a methyl pyridinium substituent of the formula $$-CH_2-\overset{\oplus}{N}\diagup\diagdown T$$

or a heterocyclic thiomethyl group of the formula $$-CH_2-S-Y$$

can be prepared by the well-known displacement reaction using a 3-acetoxymethyl-3-cephem-4-carboxylic acid as a substrate. The acetoxy group is displaced by a pyridine or a heterocyclic mercaptide compound (derived from the above heterocyclic thiol moiety), as illustrated in the following Scheme II:

Scheme II

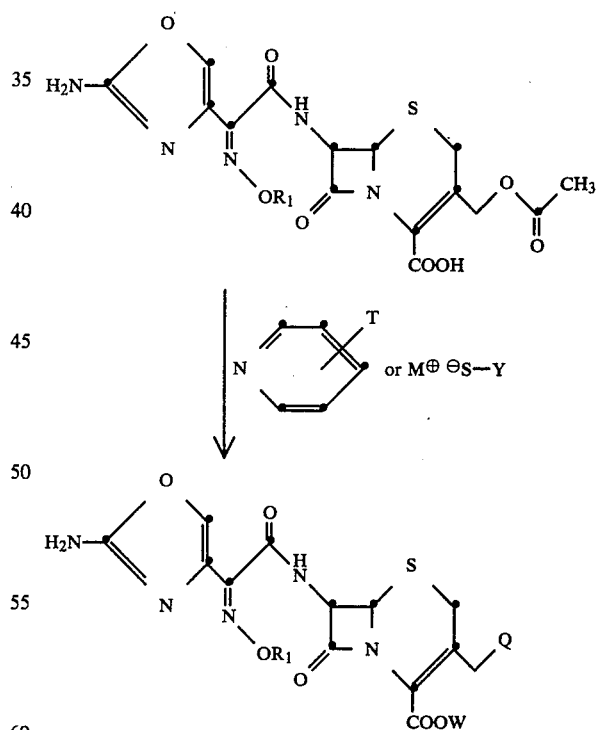

In Scheme II, R, W, Q, T and Y mean the same as they did for Scheme I.

The preparation of the 3-heterocyclicthiomethyl substituted compounds (Formula I, $R_3$ is CH—S—Y) by the displacement reaction in Scheme II is best carried out by the method of Hatfield, U.S. Pat. No. 4,144,391, issued Mar. 13, 1979. According to this method the displacement reaction is carried out under anhydrous conditions.

The preparation of 3-methyl pyridinium compounds according to the method described by Scheme II is carried out in an aqueous solvent system comprising a water miscible solvent such as acetone or acetonitrile. In general the reaction proceeds at a temperature between about 25° C. and about 65° C.

As with Scheme I, in Scheme II, it is again desirable that the nucleophilic substituents on the pyridine and on the heterocyclic mercaptide, such as carboxy, hydroxy and sulfonic acid functions, be suitably protected so as not to interfere with the displacement reactions of the nitrogen of the pyridine or the sulfur of the heterocyclic mercaptide. These protecting groups can be removed after the displacement reaction is carried out.

The synthesis of the intermedate oxime side chain compound of Formula II is an adaptation of a synthesis found in various literature references.

The general method of synthesis for the oxime side chains of the instant application is outlined by the specific synthesis of the following oxime side chain, depicted in Scheme III:

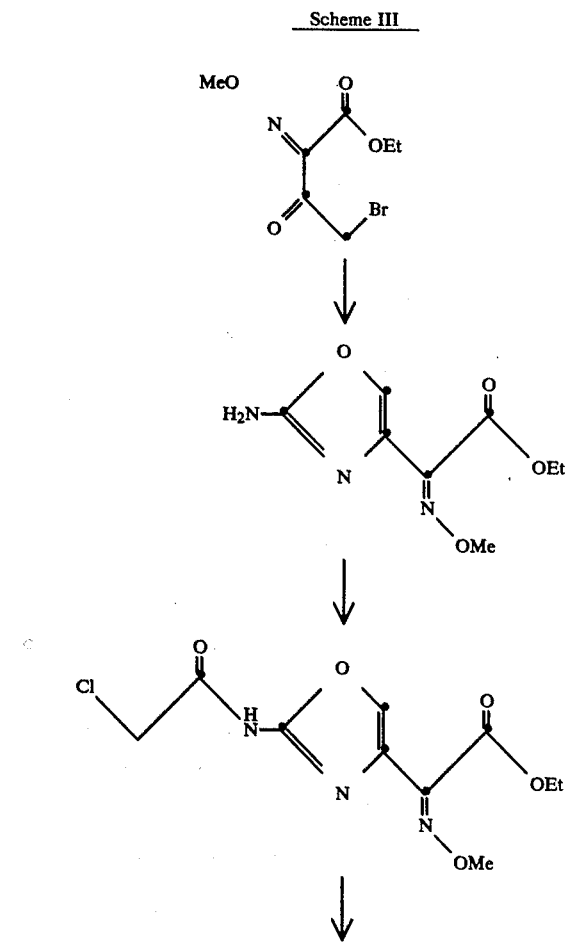

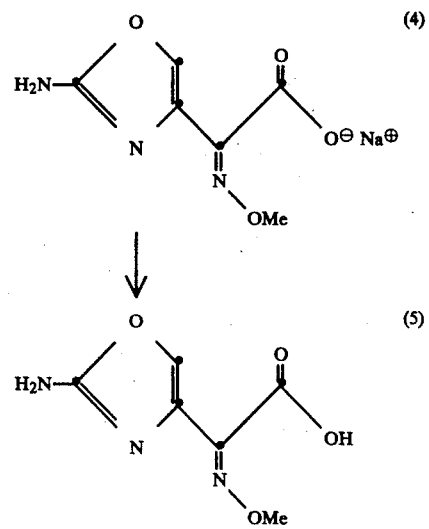

In the above Scheme III, compound 1 (ethyl-γ-bromo-α-methoximinoacetoacetate) was reacted with urea and zinc oxide in acetone or methylethylketone to give cyclized compound 2 (2-(2-amino-oxazol-4-yl)-2-Z-methoximinoacetate). Compound 2 in turn is reacted with chloroacetyl chloride in the presence of triethylamine in aqueous dimethylacetamide to give the amino-protected derivative compound 3 (ethyl 2-[2-(2-chloroacetamido)oxazol-4-yl]-2-Z-methoximinoacetate). Compound 3 is then saponified to the sodium carboxylate salt with aqueous sodium hydroxide solution and converted to the free carboxylic acid upon acidification with a suitable acid, e.g. hydrochloric acid.

The preparation of the oxime side chain (Formula II) wherein $R_1$ is a carboxy-substituted alkyl or carboxy-substituted cycloalkyl group of the formula

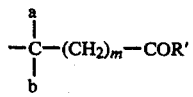

(wherein a, b, m and R' mean the same as for Formula I above) is accomplished by alkylation of the oxime group of the oxime side chain precursor represented by Formula VI,

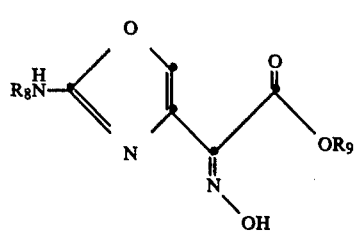

(wherein $R_9$ is a carboxy-protecting group and $R_8$ is an amino-protecting group), and a group of the Formula VII

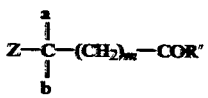

(wherein a, b and R' is as described for the compound of Formula I and Z is chloro, bromo, iodo, sulfate or sulfonate such as tosylate), followed by removal of the carboxy-protecting $R_9$ and the amino-protecting group $R_3$. The alkylation reaction is generally carried out in the presence of a base, e.g. potassium carbonate or sodium hydride, and is preferably conducted in an organic solvent, for example, dimethylsulfoxide, a cyclic ether such as tetrahydrofuran or dioxan, or an N,N-disubstituted amide such as dimethylformamide.

The preferred cephalosporin compounds of Formula I include:
benzhydryl 7β-[2-[2-(aminooxazol)-4-yl]-2-Z-methoximinoacetamido]-3-acetoxymethyl-3-cephem-4-carboxylate, 7β-[2-[(2-aminooxazol)-4-yl]-B 2-Z-methoximinoacetamido]-3-acetoxymethyl-3-cephem-4-carboxylic acid, 7β[(2-(2-aminooxazol)-4-yl]-2-Z-methoxyiminoacetamido]-3-methylpyridinium-3-cephem-4-carboxylate, Benzhydryl 7β-[2-[(2-aminooxazol)-4-yl]-2-Z-methoximinoacetamido]-3-cephem-4-carboxylate, 7β-[2-[(2-aminooxazol)-4-yl]-2-Z-methoxyiminoacetamido]-3-cephem-4-carboxylate, Benzhydryl 7β-[2-[(2-aminooxazol)-4-yl]-2-Z-methoximinoacetamido]-3-(2,5-dihydro-2-methyl-5-oxo-6-hydroxy-as-triazin-3-thiomethyl)-3-cephem-4-carboxylate, and 7β-[2-[(2-aminooxazol)-4-yl]-2-Z-methoxyiminoacetamido]-3-(2,5-dihydro-2-methyl-5-oxo-6-hydroxy-astriazin-3-thiomethyl)-3-cephem-4-carboxylic acid.

More preferred cephalosporin compounds include:
benzhydryl 7β-[2-[(2-aminooxazol)-4-yl]-2-Z-methoximinoacetamido]-3-acetoxymethyl-3-cephem-4-carboxylate, 7β-[2-[(2-aminooxazol)-4-yl]-2-Z-methoxyiminoacetamido]-3-acetoxymethyl-3-cephem-4-carboxylic acid, and 7β-[2-[(2-aminooxazol)-4-yl]-2-Z-methoxyiminoacetamido]-3-methylpyridinium-3-cephem-4-carboxylate.

The cephalosporin compounds claimed in the instant application (represented by Formula I above), either as free carboxylic acids, non-toxic pharmaceutically acceptable salt, of the carboxylic acid the hydrates of said salt, the non-toxic metabolically labile esters, with or without the acid addition form at the 2-amino position of the oxazolyl ring, are useful for treating infections in warm-blooded animals caused by gram-positive and by gram-negative bacteria. The compounds can be administered parenterally using pharmaceutically acceptable formulations.

The antibiotic compounds of the formula (wherein $R_2$ is H, or a metabolically labile ester), or the pharmaceutically acceptable, non-toxic salts thereof can be administered in an effective dose of between about 50 mg to about 2.5 g in the treatment and control of infectious diseases. The particular dosage regime may vary depending on such factors as the nature of the infection; the severity of the disease, the general health and age of the patient as well as the tolerance of the individual patient to the antibiotic. For example, the antibiotic may be administered two or more times per day and such treatment may extend for several days to two weeks or longer if necessary. The compounds can be administered intramuscularly or intravenously. For the i.v. route the compounds can be administered by the drip method whereby a pharmaceutical formulation comprising the antibiotic and a physiologically acceptable diluent is infused. Pharmaceutically acceptable diluents include, for example, 5% dextrose, 0.9% saline, Ringer's solution or other suitable diluents.

These compounds can also be administered as veterinary compositions, such as, for example, in the feed or drinking water of farm animals to treat infections such as colibacillosis or swine dysentery.

Alternatively, these compounds can be used as surface disinfectants. Solutions containing as little as 0.1 percent by weight of the antibiotic are effective for disinfecting purposes. Such solutions, preferably also containing a detergent or other cleansing agent, are useful for disinfecting objects such as glassware, dental and surgical instruments, and surfaces such as walls, floors, and tables in areas where maintenance of sterile conditions is important, i.e. hospitals, food-preparation areas, and the like.

The antibacterial activity of the compounds of this invention is illustrated by the following in vitro and in vivo test data obtained with representative compounds. In Table I, the minimum inhibitory concentration (MIC) for a representative compound against a wide range of gram-positive and gram-negative bacteria is presented. The MIC values were obtained by the standard agar dilution test.

TABLE 1

Antibiotic Activity of 7β-[2-(2-Aminooxazol-4-yl)-2-(Z-Methoximino)acetamido-3-Acetoxymethyl-3-Cephem-4-Carboxylic Acid vs. Gram-Positive and Gram-Negative Bacteria

| Test Organism* | a | b | c | d | e | f | g | h | i | j | k | l | m | n | o | p | q |
|---|---|---|---|---|---|---|---|---|---|---|---|---|---|---|---|---|---|
| Minimum Inhibitory Concentration (mcg/ml) | 2 | 4 | 128 | 16 | 4 | 64 | 0.03 | 0.015 | >128 | 32 | 0.125 | 0.125 | 0.25 | 0.5 | 0.125 | 0.06 | 0.03 |

| Test Organism* | r | s | t | u | v | w | x | y | z | a' | b' | c' | d' | e' | f' | g' | h' | i' |
|---|---|---|---|---|---|---|---|---|---|---|---|---|---|---|---|---|---|---|
| Minimum Inhibitory Concentration | 64 | 0.125 | 0.5 | 0.5 | 1 | >128 | 0.25 | 0.5 | 128 | 64 | 128 | 8 | 16 | 2 | 0.125 | 0.015 | 0.5 | 8 |

TABLE 1-continued

Antibiotic Activity of 7β-[2-(2-Aminooxazol-4-yl)-2-
(Z-Methoximino)acetamido-3-Acetoxymethyl-3-Cephem-4-
Carboxylic Acid vs. Gram-Positive and Gram-Negative Bacteria (mcg/ml)

a *Staphylococcus aureus* X1.1
b *Staphylococcus aureus* V41
c *Staphylococcus aureus* X400
d *Staphylococcus aureus* S13E
e *Staphylococcus epidermidis* EPI1
f *Staphylococcus epidermidis* EPI2
g *Streptococcus pyogenes* C203
h *Streptococcus pneumoniae* Park
i *Streptococcus* group D X66
j *Streptococcus* group D 9960
k *Hemophilus influenzae* C.L.
l *Hemophilus influenzae* 76
m *Shigella sonnei* N9
n *Escherichia coli* N10
o *Escherichia coli* EC14
p *Escherichia coli* TEM
q *Klebsiella pneumoniae* X26
r *Klebsiella pneumoniae* KAE
s *Enterobacter aerogenes* X68
t *Enterobacter aerogenes* C32
u *Enterobactor aerogenes* EB17
v *Enterobacter cloacae* EB5
w *Enterobacter cloacae* 265A
x *Salmonella heidelberg* X514
y *Salmonella typhimurium* 1335
z *Pseudomonas aeruginosa* X528
a' *Pseudomonas aeruginosa* X239
b' *Pseudomonas aeruginosa* Ps18
c' *Serratia marcescens* X99
d' *Serratia marcescens* SE3
e' *Proteus morganii* PR15
f' *Proteus inconstans* PR33
g' *Proteus rettgeri* PR7
h' *Proteus rettgeri* C24
i' *Citrobacter freundii* CF17

EXPERIMENTAL SECTION

In the following experimental procedure, the references to "dry column silica gel column chromatography" embodies the following general procedure:

Dry column silica gel (I.C.N. Nutritional Biochemicals) is poured into a column fitted with a fritted Büchner funnel and stopcocks at one end. An additional amount of this dry column silica gel, to which the compound to be chromatographed has been absorbed, is added to the top of the column. A paper filter disc is placed at the top of the column and the desired eluting solvent mixture is started through the column. The eluant was collected in 25 ml. fractions. The progress of the seperation is followed by thin layer chromatography and the fractions are combined when appropriate.

The abbreviations THF, v:v, and h. stand for tetrahydrofuran, volume to volume, and hours, respectively.

The abbreviations m.p., u.v., i.r., n.m.r. and m.s. stand for melting point, ultraviolet spectra, infrared spectra, nuclear magnetic resonance spectra and mass spectra, respectively. In addition, the absorption maxima listed for the i.r. spectra are only those of interest and not all of the maxima observed.

In conjunction with the n.m.r. spectra, the following abbreviations are used: "s" is singlet, "d" is doublet, "dd" is doublet of doublets, "br. s" is broad singlet, "t" is triplet, "q" is quartet, "m" is multiplet. "J" indicates the coupling constant in Hertz. "DMSO/d$_6$" is dimethyl sulfoxide where all protons have been replaced with deuterium.

The n.m.r. spectra were obtained on a Varian associates EM-390 90 MHz or a Jeol FT 90Q instrument. The chemical shifts are expressed in δ values (parts per million downfield from tetramethylsilane).

EXAMPLE 1

Preparation of 2-[(2-aminooxazol-4-yl]-2-Z-methoximinoacetic acid

Step A

Preparation of ethyl 2-[2-aminooxazol-4-yl]-2-methoximinoacetate

Method 1

Zinc oxide (0.406 g, 5 mmol) was suspended in a mixture composed of urea (3 g, 50 mmol) and ethyl-γ-bromo-α-methoximinoacetate (2.52 g, 10 mmol) in acetone (100 ml), and this mixture was filtered through super-cel, then was concentrated, dissolved in ethyl acetate, and the ethyl acetate solution was washed with 5% aqueous sodium bicarbonate solution and water (2×). The solution was then dried over magnesium sulfate, filtered, and concentrated in vacuo. The unreacted bromoketone was removed by trituration with ether and hexane. The residue was crystallized from 2B-ethanol to yield 0.015 g of ethyl 2-[2-aminooxazol-4-yl]-2-Z-methoximinoacetate; melting point 138°–140° C., and this compound had an n.m.r. spectrum similar to the spectrum for the product in Method 3, infra. The mother liquors from the ethanol crystallization were used as described in Method 3, infra.

Method 2

Zinc oxide (0.812 g, 10 mmol) was suspended in a mixture composed of urea (3 g, 50 mmol) and ethyl-γ-bromo-α-methoximinoacetoacetate (2.52 g, 10 mmol) in acetone (100 ml) and stirred under reflux for 85 hours. The reaction mixture was allowed to cool to room temperature, was filtered, and the filtrate was concentrated in vacuo. The residue was partitioned between ethyl acetate and 5% aqueous sodium bicarbonate solution. After washing the solution with water (2×), the ethyl acetate solution was extracted with 1 N hydrochloric acid. The acidic aqueous layer was washed with fresh ethyl acetate, then layered with ethyl acetate and made basic by the addition of aqueous sodium bicarbonate solution. The combined ethyl acetate extracts were dried over magnesium sulfate, filtered and evaporated. The residue was crystallized from (2B ethanol) yielding 0.010 g of the same product as isolated in Method 1. The mother liquors from the ethanol crystallization were used as described in Method 3, infra.

Method 3

The reaction was run as in Method 1, using 25.2 g (100 mmol) of ethyl-γ-bromo-α-methoximinoacetoacetate, 30 g (500 mmol) of urea, 4.06 g (50 mmol) of zinc oxide and substituting methylethylketone (1000 ml) for acetone. The product obtained from the 2B-ethanol crystallization was recrystallized from isopropanol to yield approximately 800 mg of the product, ethyl-2-[2-aminooxazol-4-yl]-2-methoximinoacetate. This material was combined with the crystalline lots from Methods 1 and 2, recrystallized from isopropanol to give 0.671 g of the desired product.

The mother liquors from the crystallization (ethanol) and recrystallization (isopropanol) were combined with the mother liquors of the crystallizations of Methods 1 and 2, evaporated, and the residue was chromatographed over dry column alumina, using ethyl acetate as the eluant. The fractions containing predominantly the desired product were recombined and rechromatographed as above, and the fractions containing pure product were recrystallized from isopropyl alcohol, to yield 0.1 g of ethyl 2-[2-amino-4-yl]-2-Z-methoximinoacetate; n.m.r. (CDCl$_3$) δ1.4 (t, 3, C$\underline{H}_3$CH$_2$), 4.0 (s, 3, CH$_3$O), 4.4 (q, 2, CH$_3$C$\underline{H}_2$—), 5.67 (br, s, 2, amino), 7.3 (s, 1, oxazole aromatic); i.r. (KBr) 1870 cm$^{-1}$; u.v. (methanol) λ$_m$=217 nm (ε$_m$=18,873), λ$_m$=275 nm (ε$_m$=3370); m.s. M$^+$=213; Analysis: Calculated for: C$_8$H$_{11}$N$_3$O$_4$: C, 45.07; H, 5.20; N, 19.71. Found: C, 45.05; H, 5.37; N, 19.40.

Method 4

Ethyl γ-bromo-α-methoximinoacetoacetate (100 g, 0.397 mmol), urea (91 g, 1.98 mmol), and zinc oxide (16 g, 0.198 mmol) were dissolved in methylethylketone (3 l) and the solution was stirred under reflux for 48 hours then allowed to cool. The solution was filtered and concentrated in vacuo. The dark residue was dissolved in ethyl acetate and filtered. The filtrate was evaporated in vacuo and the residue was chromatographed over activity III neutral alumina. The column was eluted sequentially with neat cyclohexane (1000 ml), 1:9 v:v ethyl acetate:cyclohexane (1000 ml), 2:8 v:v ethyl acetate:cyclohexane (2000 ml), 3:7 v:v ethyl acetate:cyclohexane (500 ml), and finally with 1:1 v:v ethyl acetate:cyclohexane until no more product was eluted. Fifty-five fractions were taken, although fractions 51 through 55 were 500 ml or greater. The crude product was contained in fractions 51, 52, and 53. The three fractions were evaporated to give a semi-crystalline mass, each of which were triturated with ether and filtered to yield 3 pure crops of crystals of product. These crops of crystals were combined with a second crop of crystals obtained from fraction B 52 to yield 8.9 g of ethyl 2-[2-aminooxazol-4-yl]-2-Z-methoximinoacetate, which gave an n.m.r. spectrum similar to the spectrum obtained for the product in Method 3.

Step B

Preparation of ethyl 2-[2-(2-chloroacetamido)-oxazol-4-yl]-2-Z-methoximinoacetate

Method 1

A mixture of ethyl 2-[2-aminooxazol-4-yl]-2-Z-methoximinoacetate (2.13 g, 10 mmol), triethylamine (1.53 ml, 11 mmol) and aqueous dimethylacetamide solution (25 ml) were chilled to 0° C. with an ice bath. A dimethylacetamide solution (10 ml) of chloroacetyl chloride (0.939 ml, 11 mmol) was added dropwise to the stirred solution. The reaction mixture was stirred for 0.5 hour at 0° C., followed by stirring at 19 hours at room temperature. The reaction mixture was poured onto ice and the resultant mixture was extracted with ethyl acetate. The ethyl acetate was washed with water, dried over anhydrous magnesium sulfate, filtered and concentrated in vacuo. After evacuating under high vacuum for 24 hours, the residue was triturated with ether and filtered. The mother liquor was evaporated and the residue was recrystallized from carbon tetrachloride to give 0.456 g of ethyl 2-[2-(2-chloroacetamido)oxazol-4-yl]-2-Z-methoximinoacetate; m.p.; 91°-92° C., n.m.r. (CDCl$_3$) δ1.32 (t, 3-CH$_3$, J=7.5 Hz), 4.0 (s, 3, OCH$_3$), 4.1 (s, 2 Cl—C$\underline{H}_2$—), 4.37 (q, 2, —O—C$\underline{H}_2$—, J=5.7 Hz), 7.25 (s, 1, aromatic proton).

Method 2

A mixture of ethyl 2-[2-aminooxazol-4-yl]-2-Z-methoximinoacetate (3.2 g, 18.24 mmol), triethylamine (2.82 ml, 20 mmol) and dimethylacetamide (90% aqueous, 50 ml) were chilled to 0° C. by means of an ice bath. An anhydrous dimethylacetamide (12 ml) of chloroacetyl chloride (1.83 ml, 20 mmol) was added dropwise to the stirred solution. The reaction mixture was stirred for 0.5 hour at 0° C. then for 15 hours at room temperature.

The mixture was poured into ice and extracted with ethyl acetate (2×). The ethyl acetate layers were combined and were washed with water (2×), were dried over magnesium sulfate, filtered, concentrated in vacuo, then were further dried under high vacuum. The residue was triturated with ether and filtered. The filtrate was concentrated and recrystallized from carbon tetrachloride yielding 0.354 g (43%) of ethyl 2-[2-(2-chloroacetamido)oxazol-4-yl]-2-Z-methoximinoacetate. This compound had the same n.m.r. spectrum as the spectrum of the compound of Method 1, above.

Step C

Preparation of 2-[(2-aminooxazol)-4-yl]-2-Z-methoximinoacetic acid

Method 1

Sodium hydroxide (5 N, 2 equivalents plus a 10% excess, 4.6 ml, 22.86 mmol) was added dropwise to a stirred suspension of ethyl 2-[2-(chloroacetamido)-oxazol-4-yl]-2-Z-methoximinoacetate (3.0 g, 10.38 mmol) in water (90 ml). Dissolution of the ester was complete within about 15 to 20 minutes, and the stirring was continued for an additional hour. The mixture was chilled and acidified by the dropwise addition of 1 N hydrochloric aicd (6 ml). The aqueous layer was saturated with sodium chloride and the mixture was saturated with large quantities of ethyl acetate. The ethyl acetate extracts were dried over anhydrous sodium sulfate, filtered, combined and concentrated in vacuo, yielding 0.453 g of 2-[(2-aminooxazol)-4-yl]-2-Z-methoximinoacetic acid; melting point; 170°–174° C. (decomposed), n.m.r. (DMSO/$d_6$) δ3.84 (s, 3, NOCH$_3$), 6.77 (br, s, 2, amino), δ7.48 (s, 1, aromatic proton).

Method 2

Ethyl 2-[2-(chloroacetamido)oxazol-4-yl]-2-Z-methoximinoacetate (1.74 g, 5.95 mmol) was suspended in water and the suspension was chilled in an ice bath. Sodium hydroxide (5 N, 2.6 ml, 13.09 mmol) was added and stirring was continued as the material slowly went into solution. After 1.5 hours of stirring at 0° C., the solution was allowed to slowly come to room temperature. This aqueous solution was then treated with XAD resin (8 ml, 1.7 mmol/ml) and stirred for 2 minutes. The solution was filtered and the resin was washed with water (5 ml) and the aqueous filtrate was lyophilized to yield 0.812 g of 2-(2-aminooxazol-4-yl)-2-Z-methoximinoacetic acid, which had the same n.m.r. spectrum as the spectrum of the product in Method 1.

EXAMPLE 2

Preparation of Benzhydryl 7β-[2-[(2-aminooxazol)-4-yl]-2-Z-methoximinoacetamido]-3-acetoxymethyl-3-cephem-4-carboxylate 2-(2-Aminooxazol-4-yl)-2-(Z-methoximino) acetic acid (0.261 g, 1 mmol) was dissolved in a mixture of dimethylacetamide (3 ml) and methylene chloride (3 ml). Triethylamine (0.139 ml, 1 mmol) was added to this solution, then the resultant mixture was added dropwise to a stirred, chilled methylene chloride (25 ml) of isobutyl-chlorocarbonate. This reaction mixture was stirred for 1 hour, at the end of which time a methylene chloride (5 ml) solution of benzhydryl 7β-amino-3-acetoxymethyl-3-cephem-4-carboxylate was added dropwise. Initially, the resultant reaction mixture was stirred at 0° to 10° C. but was allowed to gradually warm to ambient temperature and stirring was continued overnight.

The solvent from the reaction mixture was removed in vacuo and the residue was taken up in ethyl acetate. The ethyl acetate solution was washed sequentially with 1 N hydrochloric acid, 10% aqueous sodium bicarbonate, and saturated aqueous sodium chloride solution. Removal of the ethyl acetate solvent in vacuo, after drying the solution over sodium sulfate and filtering, resulted in a yellow foam. This crude product mixture was chromatographed over Activity III Silica Gel (100–200 mesh, Woehlm). Elution was begun with 7:3 v:v ethyl acetate:cyclohexane (fractions 1 through 9), then neat ethyl acetate (fractions 20 through 34), and finally 9:1 v:v ethyl acetate:methanol (fractions 34 through 37). The desired product, benzhydryl 7β-[2-[(2-aminooxazol)-4-yl]-2-Z-methoximinoacetamido]-3-acetoxymethyl-3-cephem-4-carboxylate, was contained in fractions 14 through 30, and these fractions combined to yield 0.100 g of the desired product: n.m.r. (CDCl$_3$) δ1.98 (s, 3, methyl of 3-acetoxymethyl), 3.3 and 3.56 (ABq, 2, C-2), 4.75 and 5.01 (ABq, 2, C-3′), 5.02 (d, 1, C-6), 5.25 (br, s, 2, amino), 5.95 (q, 1, C-7), 7.91 (s, 1, benzhydryl methine proton), 7.3 (m, 11, phenyl rings and oxazole ring), 8.42 (d, 1, amido proton).

EXAMPLE 3

Preparation of 7β-[2-[(2-aminooxazol)-4-yl]-2-Z-methoximinoacetamido]-3-acetoxymethyl-3-cephem-4-carboxylic acid Benzhydryl 7β-[2-[(2-aminooxazol)-4-yl]-2-Z-methoximinoacetamido]-3-acetoxymethyl-3-cephem-4-carboxylate (approximately 100 mg, 0.16 mmol) was dissolved in a mixture of formic acid (97–100%, 4 ml) and triethylsilane (0.04 ml, 0.25 mmol), and this reaction mixture was stirred at room temperature for 3 hours. The reaction mixture was diluted with ethyl acetate, evaporated to gum, and the gum was purged with an ethyl acetate/acetonitrile mixture (2×) to give a light brown powder. This powder was further dried by evaporation in vacuo for 1 hour. The brown powder was then dried with ether for 0.5 hour, sonnicated, filtered and air-dried to yield 64 mg (91%) of 7β-[2-[(2-aminooxazol)-yl]-2-Z-methoximinoacetamido]-3-acetoxymethyl-3-cephem-4-carboxylic acid; n.m.r. (DMSO/$d_6$)δ, 3.4 (m, 2, C-2), 3.85 (s, 3, =NOCH$_3$), 4.85 (q, 2, J=16, C-3′), 5.15 (d, 1, J=6, C-6), 5.8 (q, 1, J=4, C-7), 6.85 (s, 2, amino), 7.5 (s, 1, oxazole ring), 9.6 (d, 1, J=9, amido).

EXAMPLE 4

Preparation of 1-(N-oxide)benzotriazol-3-yl 2-[2-aminooxazol-4-yl]-2-Z-methoximinoacetamide A mixture of 1-hydroxybenzotriazole monohydrate (1.02 g, 6.68 mmol) and triethylamine (1.14 ml, 8.16 mmol) in dimethylacetamide (8 ml) was chilled in an ice-acetone bath and a dimethylacetamide (2 ml) solution of methanesulfonyl chloride (0.57 ml, 7.3 mmol) was added dropwise. Stirring of the resultant solution at 0° to 10° C. was continued for 1.5 hours.

2-[2-Aminooxazol-4-yl]-2-Z-methoximinoacetic acid (1.235 g, 6.68 mmol), dissolved in dimethylacetamide (2.5 ml), together with triethylamine (1.01 ml) was then added dropwise to the reaction mixture, and the solution was stirred at 0° to 10° C. for an additional 1.5 hours. Water (21 ml) was then added in a dropwise fashion, resulting in the formation of a precipitate shortly following the addition. Within 10 minutes after the water had been added, the precipitate formed, was collected by filtration, was washed with cold water, and was dried in vacuo to yield 1.277 g (63%) of 1-(N-oxide)benzotriazol-3-yl 2-[2-aminooxazol-4-yl]-2-Z-methoximinoacetamide: n.m.r. (CDCl$_3$ plus DMSO/$d_6$, obtained from the same product of another procedure) δ3.90 (s, 3, —OCH$_3$), 5.95 (br. s, 2, amino), 7.43 (s, 1, oxazole proton), 7.45–8.1 (m, 3, the C-5, 6, and 7 protons of the benzotriazole moiety), 8.45 (d, 1, the C-4 proton of the benzotriazole moiety).

EXAMPLE 5

Preparation of 7β-[2-[2-aminooxazol-4-yl]-2-Z-methoximinoacetamido]-3-acetoxymethyl-3-cephem-4-carboxylic acid 7β-Amino-3-acetoxymethyl-3-cephem-4-carboxylic acid (0.43 g, 1.58 mmol) was suspended in a 1:1 v:v water:acetone solvent (25 ml) and triethylamine (0.2 ml, 1.48 mmol) was added dropwise to the stirred solution, which was cooled in an ice bath. After the cephalosporin substrate was in solution, 1-(N-oxide)benzotriazol-3-yl 2-[2-aminooxazol-4-yl]-2-Z-methoximinoacetamide (0.5 g, 1.66 mmol) was added portionwise. The pH of this solution was maintained at approximately 7.5 by the periodic additions of 45% aqueous potassium phosphate solution. After the addition of the benzotriazole amide was complete, the mixture was slowly allowed to warm to room temperature. After approximately 2 hours, dissolution had occurred and stirring of the solution was continued overnight. The acetone was removed, and the aqueous solution was diluted with water, layered with ethyl acetate, and the pH of the solution was adjusted to pH 2.5 by the addition of 1 N hydrochloric acid. The ethyl acetate layer was then separated, dried over magnesium sulfate, filtered and evaporated in vacuo. The residue was partially crystalline, and the residue was then triturated with ether and filtered to yield 0.3 g of 7β-[2-[2-aminooxazol-4-yl]-2-Z-methoximinoacetamido]-3-acetoxymethyl-3-cephem-4-carboxylic acid: n.m.r. (DMSO/d₆) δ2.0 (s, 3, OAc), 3.32 and 3.61 (ABq, 2, J=18 Hz, C-2 protons), 4.85 (s, 3, OCH₃), 4.7 and 5.0 (ABq, 2, J=12 Hz, C-3′ protons), 5.08 (d, 1, J=4.5 Hz, C-6 proton), 5.72 (q, 1, J=4.5 and 9 Hz, C-7 proton), 6.6 (br. s, 2, amino), 7.38 (s, 1, oxazole aromatic proton), 9.5 (d, 1, J=9 Hz, 7-amido N-proton); u.v. (methanol) λmax=217 ($\epsilon_m$=19,254), λmax=265 ($\epsilon_m$=10,200);

Analysis: Calculated: C, 43.74; H, 3.90; N, 15.94. Observed: C, 44.01; H, 3.97; N, 15.75.

EXAMPLE 6

Preparation of 1-(N-oxide)benzotriazol-3-yl 2-[(2-aminooxazol)-4-yl]-2-Z-methoximinoacetamide Methanesulfonyl chloride (0.046 ml, 0.059 mmol) was dissolved in dimethylacetamide (0.46 ml). This solution was diluted to a total of 1 ml with additional dimethylacetamide and an aliquot (0.1 ml) of this diluted solution was added dropwise to a cold (0° to 10° C.), stirring dimethylacetamide (0.65 ml) solution of triethylamine (0.092 ml, 0.66 mmol) and 1-hydroxybenzotriazole monohydrate (0.08 ml, 27 g, 0.54 mmol). The resultant mixture was stirred for 1.5 hours. 2-(Aminooxazol-4-yl)-2-Z-methoximinoacetic acid (0.1 g, 0.54 mmol) was added to this mixture followed by the addition of a dimethylacetamide (0.2 ml) solution of triethylamine (0.082 ml) and this mixture was stirred for 1.5 hours. Water (1.7 ml) was added dropwise causing a precipitate to form. The precipitate was collected by filtration then air dried under vacuum to give 0.1 g of 1-[N-oxide]-benzotriazol-3-yl 2-[(2-aminooxazol)-4-yl]-2-Z-methoximinoacetamide. n.m.r. (CDCl₃ plus DMSO/d₆) δ3.90 (s, 3, —OCH₃), 5.95 (m, 3, the 5, 6, and 7 protons of the benzotriazole group), 8.45 (d, 1, the 4 proton of the benzotriazole group).

EXAMPLE 7

Preparation of 7β-[2-[(2-aminooxazol-4-yl]-2-Z-methoximinoacetamido]-3-methylpyridinium-3-cephem-4-carboxylate 7β-Amino-3-methylpyridinium-3-cephem-4-carboxylic acid chloride (0.134 g, 0.364 mmol) was suspended in acetone/water (1.6 ml/1 ml) and the pH of this suspension was adjusted to approximately 7.5 by the dropwise addition of a 45% solution of potassium phosphate. 1-(N-oxide)benzotriazol-3-yl 2-[(2-aminooxazol-4-yl]-2-Z-methoximinoacetamide (0.1 g, 0.33 mmol) was added to the suspension and the resulting suspension was stirred in the cold for 2 hours, then the mixture was allowed to slowly warm to room temperature. The pH of this stirred suspension was maintained at pH 7.5 by the addition of 45% aqueous potassium phosphate solution. The suspension was stirred overnight, at the end of which time the acetone was removed in vacuo and the remaining aqueous phase was diluted with water then washed with ethyl acetate. The aqueous layer was then acidified to pH 2 by the addition of dilute hydrochloric acid, washed with ethyl acetate and evaporated to dryness. The residue was triturated with methanol and filtered. Approximately 0.1 g of this residue was purified by HPLC on a reversed phase C-18 silica gel column. The solvent system used for this chromatography was composed of 2% acetic acid, 6% acetonitrile, and the water. Approximately 0.025 g of pure 7β-[2-[(2-aminooxazol)-4-yl]-2-Z-methoximinoacetamido]-3-methylpyridinium-3-cephem-4-carboxylate was obtained. FT-n.m.r. (DMSO/d₆) δ3.42 (m, 2, C-2), 3.80 (3, s, N-OCH₃), 5.03 (d, 1, C-6), 5.08 (d, 1, C-3′), 5.7 (d, 1, C-3′), 5.64 (q, 1, C-7), 6.8 (s, 2, amino), 7.42 (s, 1, oxazole aromatic proton), 8–9.6 (m, 6, amido proton and pyridinium protons).

I claim:
1. A compound of the formula

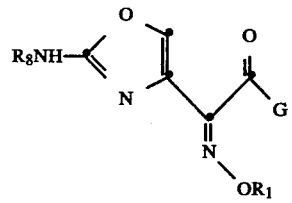

wherein:
R₁ is hydrogen, C₁ to C₄ alkyl, a carboxy-substituted alkyl or carboxy-substituted cycloalkyl group represented by the formula

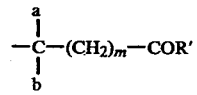

wherein m is 0 to 3; a and b when taken separately are independently hydrogen or C₁ to C₃ alkyl, or when taken together with the carbon to which they are attached form a C₃ to C₇ carboxylic ring; R′ is hydroxy, amino, C₁ to C₄ alkoxy, or —OR″ where R″ is a carboxy-protecting group; or R₁ is a secondary amido group of the formula

wherein R‴ is C₁ to C₄ alkyl, phenyl or C₁ to C₃ alkyl substituted by phenyl; R₈ is hydrogen or an amino protecting group; G is chloro, bromo, hydroxy, C₁ to C₄ alkoxy, phenoxy, or a group of the formula

wherein J is the residue of a group forming an activated ester; or a group of the formula

wherein M⊕ is a monovalent cation.
2. The compound of claim 1, wherein R₁ is C₁ to C₄ alkyl.
3. The compound of claim 2, wherein R₁ is methyl.
4. The compound of claim 1, wherein R₈ is hydrogen.
5. The compound of claim 1, wherein R₈ is an amino protecting group.
6. The compound of claim 5, wherein R₈ is chloroacetyl.

7. The compound of claim 1, wherein G is hydroxy.

8. The compound of claim 7, wherein $R_1$ is $C_1$ to $C_4$ alkyl.

9. The compound of claim 8, wherein $R_1$ is methyl.

10. The compound of claim 9, wherein $R_8$ is hydrogen.

11. The compound of claim 1, wherein G is a group of the formula

—O—J wherein J is the residue of a group forming an activated ester.

12. The compound of claim 11, wherein J is

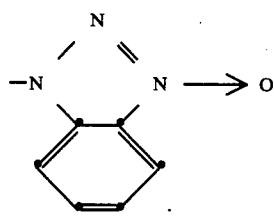

13. The compound of claim 11, wherein $R_1$ is $C_1$ to $C_4$ alkyl.

14. The compound of claim 13, wherein $R_1$ is methyl.

15. The compound of claim 14, wherein J is

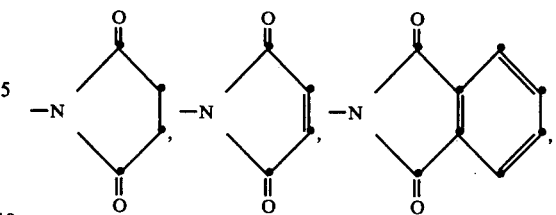

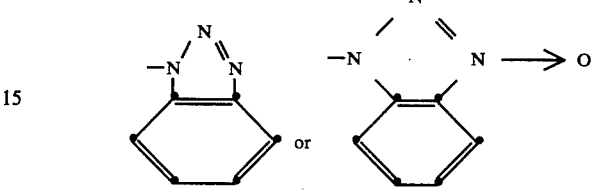

16. The compound of claim 15, wherein J is

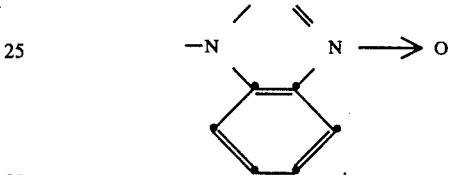

17. The compound of claim 16, wherein $R_8$ is hydrogen.

18. The compound of claim 1, wherein G is $C_1$ to $C_4$ alkoxy.

19. The compound of claim 18, wherein G is ethoxy.

20. The compound of claim 18, wherein $R_1$ is $C_1$ to $C_4$ alkyl.

21. The compound of claim 20, wherein $R_1$ is methyl.

22. The compound of claim 21, wherein G is ethoxy.

23. The compound of claim 22, wherein $R_8$ is an amino protecting group.

24. The compound of claim 23, wherein $R_8$ is chloroacetoxy.

25. The compound of claim 22, wherein $R_8$ is hydrogen.

* * * * *